(12) United States Patent
Green et al.

(10) Patent No.: US 6,547,717 B1
(45) Date of Patent: Apr. 15, 2003

(54) MULTIFACET SEXUAL AID

(76) Inventors: John P. Green, 806 Goodson St., Enterprise, AL (US) 36330; Jeffery Sigler, Rte. 1, Box 412A, Dalevill, AL (US) 36322

( * ) Notice: Subject to any disclaimer, the term of this patent is extended or adjusted under 35 U.S.C. 154(b) by 103 days.

(21) Appl. No.: 09/712,982

(22) Filed: Nov. 16, 2000

Related U.S. Application Data

(60) Provisional application No. 60/218,801, filed on Jul. 18, 2000.

(51) Int. Cl.[7] .................................................. A61F 5/00
(52) U.S. Cl. ...................................................... 600/38
(58) Field of Search ................. 600/38–41; 403/DIG. 4

(56) References Cited

U.S. PATENT DOCUMENTS

| | | | |
|---|---|---|---|
| 2,899,957 A | | 8/1959 | Briggs |
| 3,375,381 A | | 3/1968 | Tavel |
| 3,554,184 A | | 1/1971 | Habib |
| 3,712,652 A | * | 1/1973 | Uilkema .................. 248/188.5 |
| 3,759,254 A | | 9/1973 | Clark |
| D246,119 S | | 10/1977 | Okamoto |
| 4,385,849 A | * | 5/1983 | Crain ......................... 343/901 |
| 4,488,541 A | | 12/1984 | Garcia |
| 4,643,175 A | | 2/1987 | Chapman |
| 4,989,592 A | | 2/1991 | Chang |
| 5,103,810 A | | 4/1992 | Chang |
| 5,127,396 A | | 7/1992 | McAllister |
| 5,255,993 A | * | 10/1993 | Kovacs ....................... 403/316 |
| 5,458,559 A | | 10/1995 | Gauntlett |
| 5,470,303 A | | 11/1995 | Leonard et al. |
| D371,442 S | | 7/1996 | Semyonova |
| 5,573,499 A | | 11/1996 | McAllister |
| 5,620,429 A | | 4/1997 | Al-Saleh |
| D380,547 S | | 7/1997 | Carlsen |
| 5,690,603 A | | 11/1997 | Kain |
| 5,725,473 A | | 3/1998 | Taylor |
| D395,081 S | | 6/1998 | Bowden |
| 5,842,970 A | | 12/1998 | Lakusiewicz |

FOREIGN PATENT DOCUMENTS

| | | |
|---|---|---|
| CA | 815315 | 6/1969 |
| DE | 2604511 | 8/1977 |

OTHER PUBLICATIONS

Voyages catalog, p. 49; Puritan Quarterly Journal, No. 8 Adult American Dream Book, p. 8.

* cited by examiner

*Primary Examiner*—John P. Lacyk

(57) ABSTRACT

A multifacet sexual aid device for increasing the level of sexual enjoyment between partners which includes a waist belt having a first, second and third belt portion. The first belt portion has a substantially planar portion and a first and second attachment end. The planar portion is a parabolic shaped front element which include a spring-loaded attachment mechanism within a substantially central portion of the planar portion for attaching at least one prosthetic phallic element thereto, as a quick release and quickly deployed element. A couple connector is also used to couple a plurality of different prosthetic phallic elements as either a convex or concave connection to the spring-loaded mechanism. The free ends of each second and third belt portions are fixedly secured at opposing internal first and second internal surface portions via hook and loop fasteners.

15 Claims, 17 Drawing Sheets

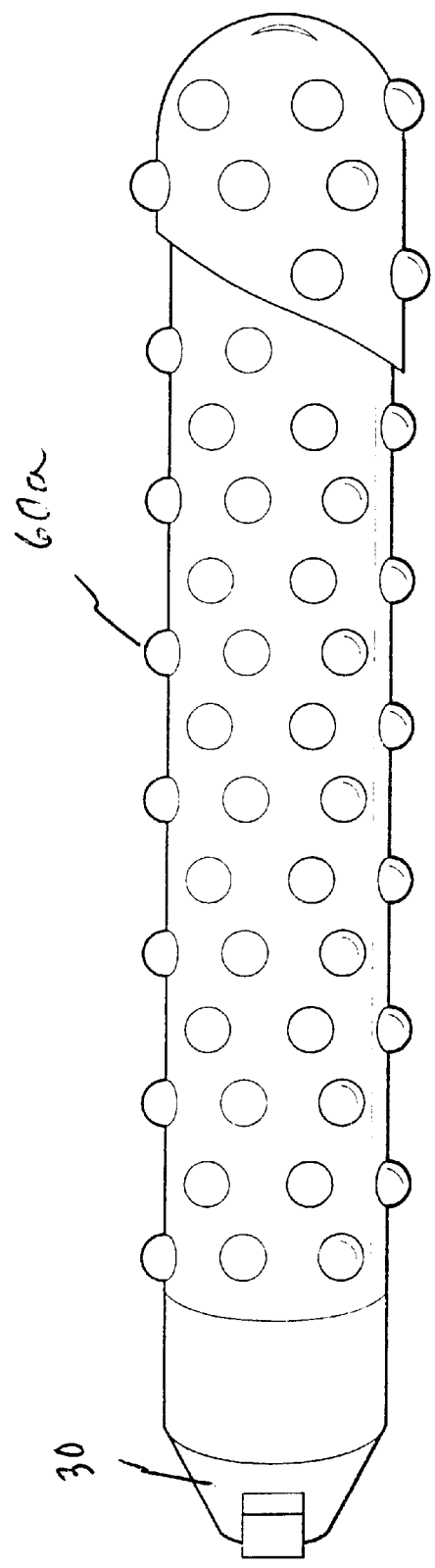

MULTIFACET SEXUAL AID

CROSS-REFERENCE TO RELATED APPLICATION

This application claims the benefit of U.S. Provisional Patent Application Serial No. 60/218,801, filed Jul. 18, 2000.

BACKGROUND OF THE INVENTION

1. Field of the Invention

The present invention relates generally to sexual appliances. More specifically, the invention is a multifacet sexual aid which enables the use of a plurality of detachable male and female prosthetic members of various configurations and/or shapes and sizes to effect heightened levels of sexual intercourse between the sexes.

2. Description of Related Art

Sexual appliances have long been used as educational tools, therapeutic devices and to prevent the transmission of communicable or sexually transmitted diseases of varying sorts. Other and probably more valid purposes for the use of sexual aids may be related to some medical or psychologically induced dysfunction suffered by a sexual partner which stymied the fullness or ecstasy of the sexual experience between two people.

Such use of sexual aids has bridged many chasms between the sexes, particularly, between husband and wives who have experienced some form of mental, physical or emotional trauma which has temporarily severed emotional or sexual ties between them. This form of trauma has the propensity to short circuit the emotional connection which is an important link when not unsevered which leads to the wonderful experience or mutual enjoyment of sexual intercourse. Among the conventional sexual aids as further described below are prosthetic phallic elements or dildos which are erogenic stimulators. One of the most debilitating problems with these types of sexual aids is the lack of a secure connection for uninterrupted use during intercourse. The multifacet sexual aid as herein described is a quick release sexual aid which is adapted for numerous prosthetic facets which effects multiple levels of sensual enjoyment between sexual partners not heretofore or hereinbelow described.

U.S. Patents issued to Briggs (U.S. Pat. No. 2,899,957), Clark (U.S. Pat. No. 3,759,254), McAllister (U.S. Pat. No. 5,127,396) and Kain (U.S. Pat. No. 5,690,603) describe the evolution of the erogenic stimulator up to a point in time around Nov. 25, 1997 where the public innately required a more secure means of utilizing prosthetic phallic elements or dildos for an extended level of use. Later came numerous fastening prosthetic devices waist belts and pubo-vaginal devices for females as described in the U.S. Patent issued to Habib (U.S. Pat. No. 3,554,184).

Similar waist belt prosthetic fasteners are disclosed in U.S. Patents issued to Garcia (U.S. Pat. No. 4,488,541), Chang (U.S. Pat. No. 4,989,592), Chang (U.S. Pat. No. 5,103,810), Taylor (U.S. Pat. No. 5,725,473) and Lakusiewicz (U.S. Pat. No. 5,842,970). One of the major set backs of the screw-on type prosthetic fasteners is the extensive time delay required to remove or exchange prosthetic elements during actual intercourse. Another failure of the conventional prosthetic sexual aids is the demand for an alternating power source to run complex mechanisms for sexual stimulation which usually amounts to electrical cord entanglements or barriers between sexual partners.

As a corrective alternative, patents respectively issued and granted to Tavel (U.S. Pat. No. 3,375,381), McAllister (U.S. Pat. No. 5,573,499) and Merz (U.S. Pat. No. CA (U.S. Pat. No. 815,315) disclose cordless sexual aids which run vibrator systems disposed within the prosthetic phallic or dildo. Other conventional features which fall within the scope of these corrective alternatives include the advent of artificial vaginas which also incorporate the use of cordless or direct current generating power sources for providing sensual stimulation via the vibratory mechanisms between partners. These features are clearly described in patents issued and granted to Gauntlett (U.S. Pat. No. 5,458,559), Leonard et al. (U.S. Pat. No. 5,470,303) and Beantragt (U.S. Pat. No. CA 2604511), respectively.

The following patents and publications by Chapman (U.S. Pat. No. 4,643,175), (U.S. Pat. No. 5,620,429), Okamoto (U.S. Pat. No. DES. 246,119), Carlsen (U.S. Pat. No. DES. 380,547), Semyonova (U.S. Pat. No. DES. 371,442), Bowden (U.S. Pat. No. DES. 395,081) and VOYAGES Catalog (undated material) disclose conventional prosthetic devices with ornamental features which are considered to be of general relevance to the multifacet sexual aid as herein described.

Thus, none of the above inventions and patents, taken either singly or in combination, is seen to describe the instant invention as claimed.

SUMMARY OF THE INVENTION

The multifacet sexual aid according to the invention includes a waist belt having a first, second and third belt portion. The first belt portion has a substantially planar portion and a first and second attachment end. The planar portion is a parabolic shaped front element which include a spring-loaded attachment mechanism within a substantially central portion of the planar potion for attaching at least one prosthetic phallic element thereto as a quick release and quickly deployed element. A couple connector is also used to couple a plurality of different prosthetic phallic elements as either a convex or concave connection to the spring-loaded mechanism.

The second and third belt portion are fixedly joined to the substantially planar portion at a common point such that the intersection of the respective ends forms insertable loops for inserting a user's legs therein. The free ends of each second and third belt portions are fixedly secured at opposing internal first and second internal surface portions of the first belt portion via mechanical stitching. The first belt portion includes hook and loop fasteners disposed on the first and second attachment ends, respectively for releasably fastening and securing the first and second ends of the first belt portion together. The spring-loaded mechanism includes both a concave configuration and a convex configuration for alternately attaching at least one prosthetic phallic member with or without the use of the coupled connector.

Accordingly, it is a principal object of the invention to provide a multifacet sexual aid for effecting heightened levels of sexual stimulation between sexual partners.

It is another object of the invention to provide a multifacet sexual aid which is easily deployed and/or removed with a minimized number of mechanical fasteners or attachments.

It is a further object of the invention to provide a multifacet sexual aid which decrease delay time between exchanging different prosthetic facets during sexual intercourse.

Still another object of the invention is to provide a multifacet sexual aid which is light-weight and impervious to moisture ladened effects such as rust and corrosion.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2C is a perspective side view of a prosthetic facet member according to a third configuration of the invention.

Similar reference characters denote corresponding features consistently throughout the attached drawings.

DETAILED DESCRIPTION OF THE PREFERRED EMBODIMENTS

Figure 1A:
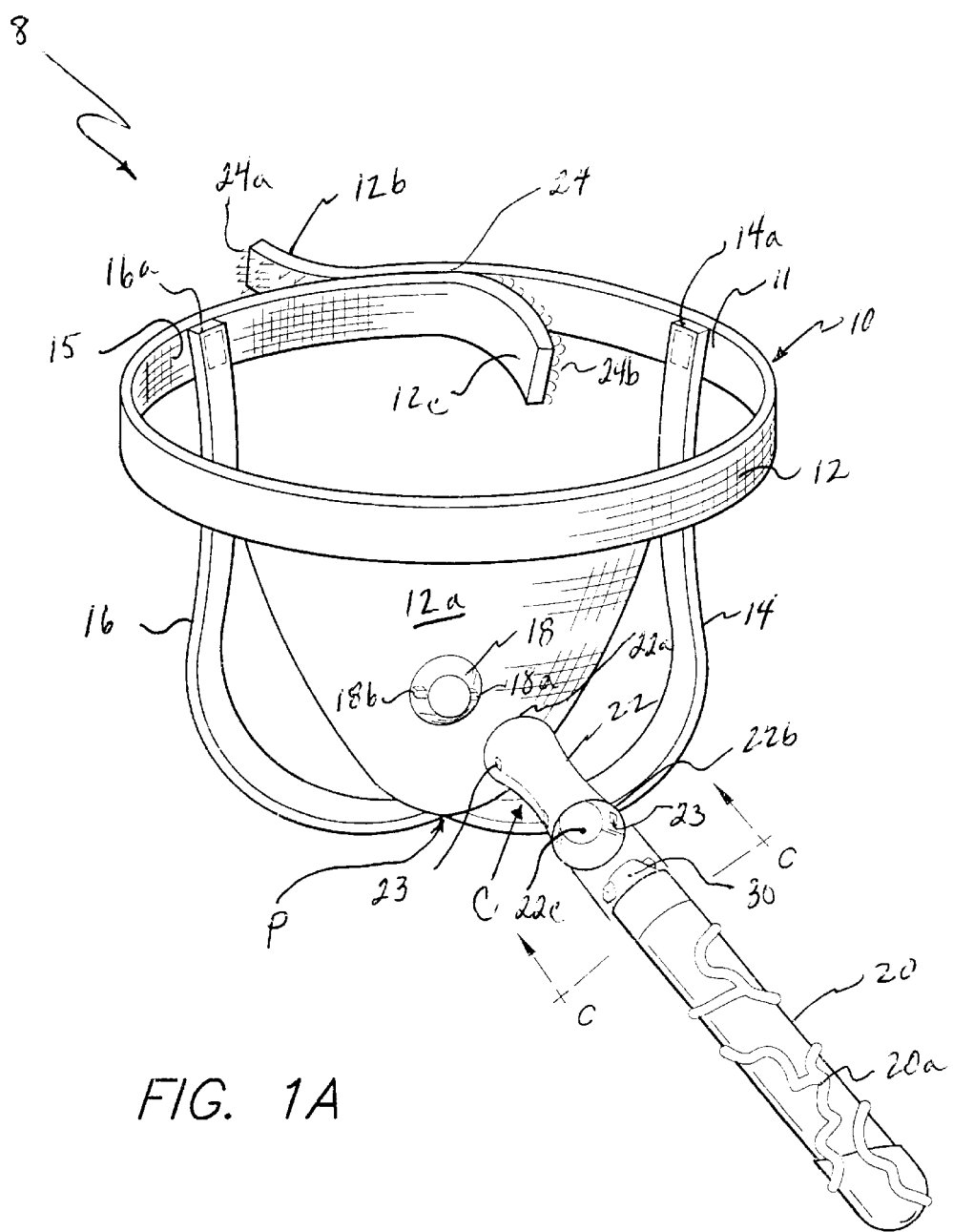
FIG. 1A is an environmental, perspective view of a multifacet sexual aid according to the present invention.
Figure 1B:
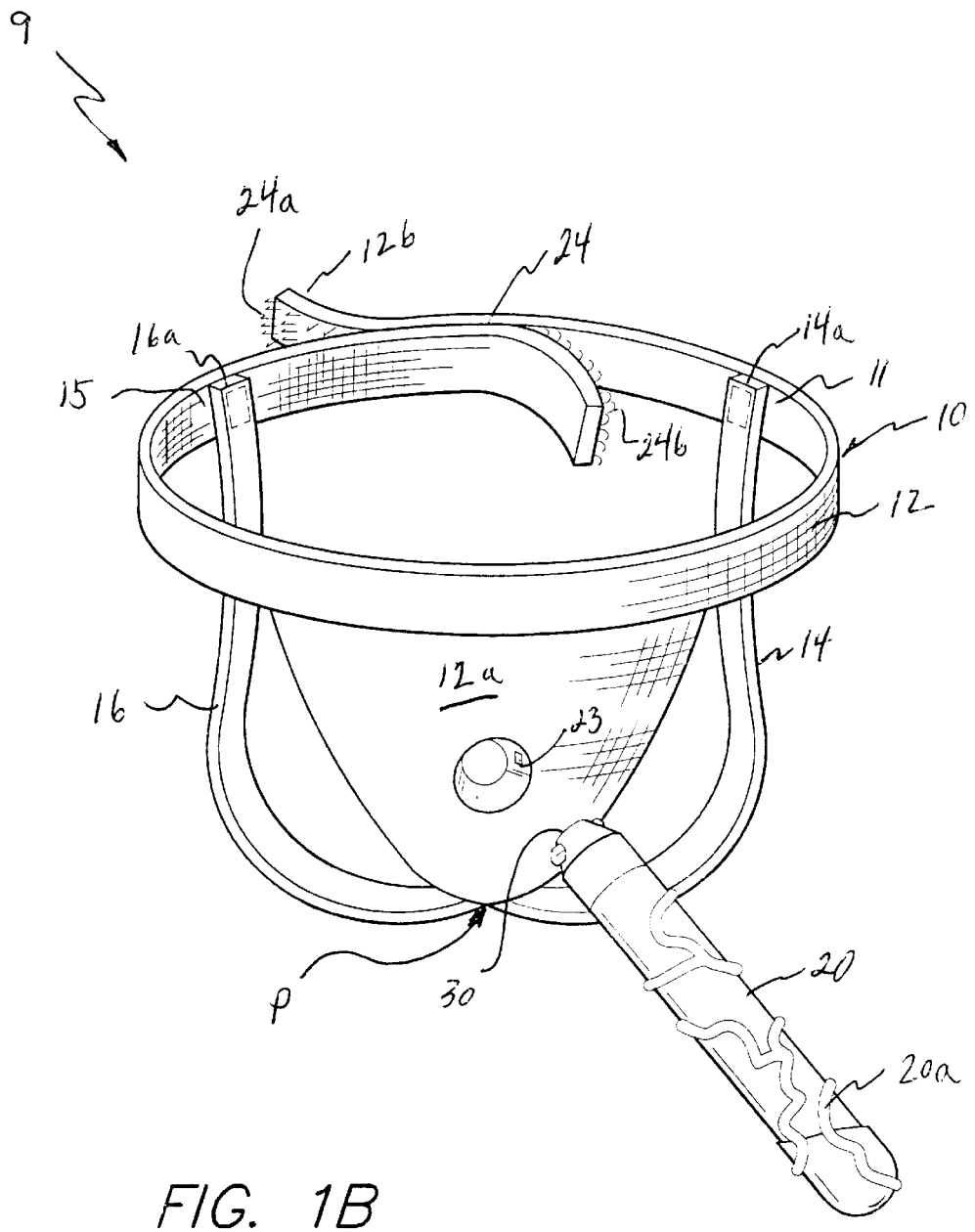
FIG. 1B is a front perspective view of the multifacet sexual aid according to a second embodiment of the invention.
Figure 1C:
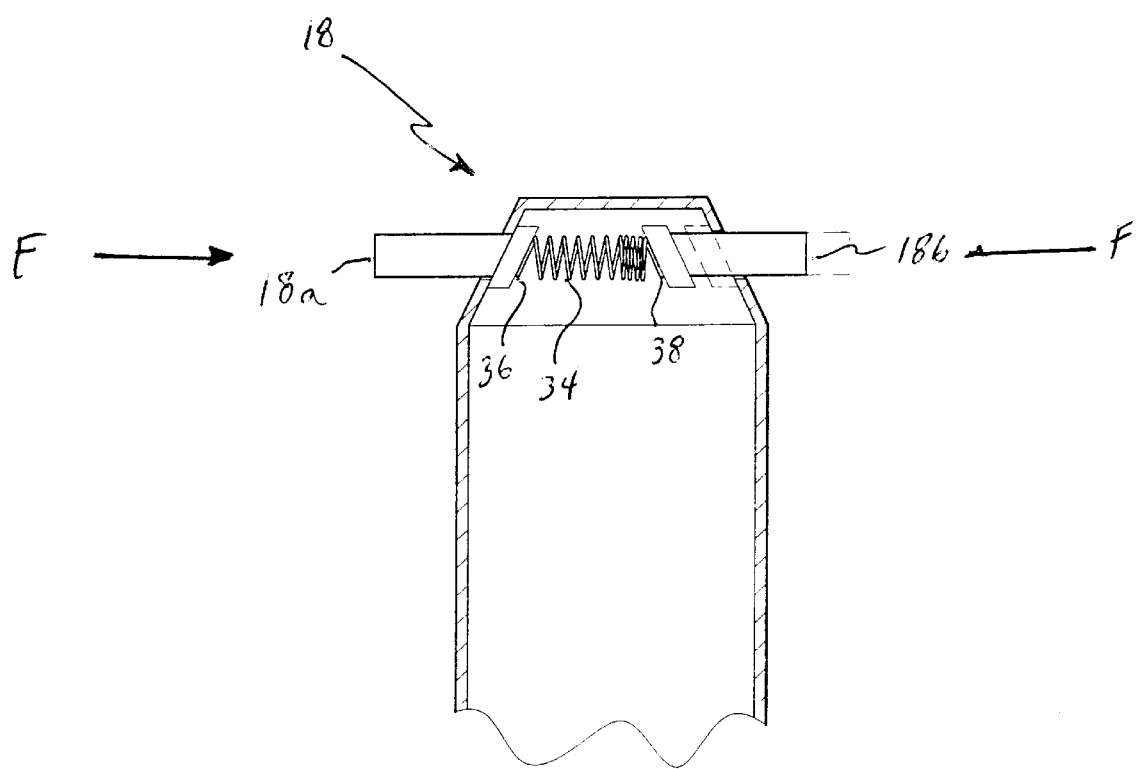
FIG. 1C is a perspective sectional view of the receptor portion of the multifacet sexual aid taken along line C—C, illustrating a spring loaded attachment mechanism.

The present invention is directed to a multifacet sexual aid. The preferred embodiments of the present invention are depicted in FIGS. 1A–1C, and a plurality of combination attachment configurations diagrammatically illustrated in FIGS. 2A–7. The preferred embodiments are generally referenced by numerals 8 and 9, respectively with combination configurations depicted in FIGS. 2A–7 sequentially and numerically designated below.

As diagrammatically illustrated in FIG. 1A, the multifacet sexual aid 8 according to the first embodiment comprises a waist belt 10 having a first 12, second 14 and third 16 belt portion.

The first belt portion 12 has a substantially planar portion 12a and a first and second end 12b,12c, respectively. The substantially planar portion 12a has a substantially parabolic shaped structure (concave up) and includes a means 18 for attaching at least one prosthetic phallic element 20 of predetermined spatial dimensions thereto (as concave to convex coupled attachment) Accordingly, a coupling means 22 is also shown therein for coupling at least one prosthetic phallic member 20 to the attachment means 18 which is preferably a spring-loaded concave mechanism 18 having a first and second attachment end 18a and 18b, respectively. The coupling means 22 is substantially cylindrical in construction but narrows in diameter near its center C. First and second ends 22a,22b form frusti-conical shaped surfaces having a set of apertures 23 therein. Intermediate each respective end 22a, 22b is an adjoining central bore 22c having a constant diameter formed therein.

The second and third belt portions 14,16 are fixedly joined to the substantially planar portion 12a at a common point P such that the intersection of the belt portions 14,16 at point P forms loops of predetermined dimensions for inserting a user's legs therein as a customized feature. The free ends 14a and 16a of the second and third belt portions 14, 16 are fixedly secured at opposing internal first and second surface portions 11 and 15 of the first belt portion 12 via mechanical stitching techniques. The first belt portion 12 further comprises a fastener means 24 for releasably fastening and securing the respective first and second ends 12b,12c of the first belt portion 12 around the waist of a user. The fastener means 24 is preferably hook 24a and loop 24b fasteners.

With respect to the attachment means 18, it is preferably a spring-loaded mechanism having first and second attachment ends 18a and 18b, respectively for insertably attaching to and receiving the at least one prosthetic phallic member 20 which include mating or compatible attachment mechanism 30 thereon.

As diagrammatically illustrated in FIG. 1B, the multifacet sexual aid 9 according to the second embodiment, is an exact replica of the first embodiment 8, except the attachment means 32 disposed within the substantially planar portion 12a is a convex receivable mechanism 32 or frusti-conically shaped structure according to an exact replica of one of the ends 22a, 22b of the coupling means 22. Accordingly, the second embodiment 9 can be utilized without the need for an adapter or coupler 22. The spring-loaded mechanism 18 is more clearly depicted in FIG. 1C, where a cut taken along line C—C of the concave shaped element reveals a spring 34 having a predetermined spring k (N/m) for effecting a spring bias or displacement according to a compressive or axial force F acting on either end 18a and 18b. The spring is mechanically fixed or secured at ends 36 and 38 by any number of available techniques so long as factors such cyclical stress and material fatigue are factored into the fastening technique.

As for both embodiments 8 and 9, FIGS. 2A–7 diagrammatically illustrate the multifacet configurations used in combination with instant invention. As depicted in FIGS. 1A and 1B, the phallic element 20 is shown comprising vein like protruding contours 20a along the peripheral surface of the element 20 according to predetermined spatial dimensions. As depicted FIG. 2A, a phallic element 40 is shown comprising a series of contiguous spherical balls 40a–40h attached end to end and decreasing in diameter thereto. As depicted in FIG. 2B, the phallic element 50 is shown comprising a series of concentric spiral contours 50a which taper in decreasing diameter thereto. As depicted in FIG. 2C, the phallic element 60 is shown comprising a plurality of bumps 60a disposed thereon.

Figure 2A:
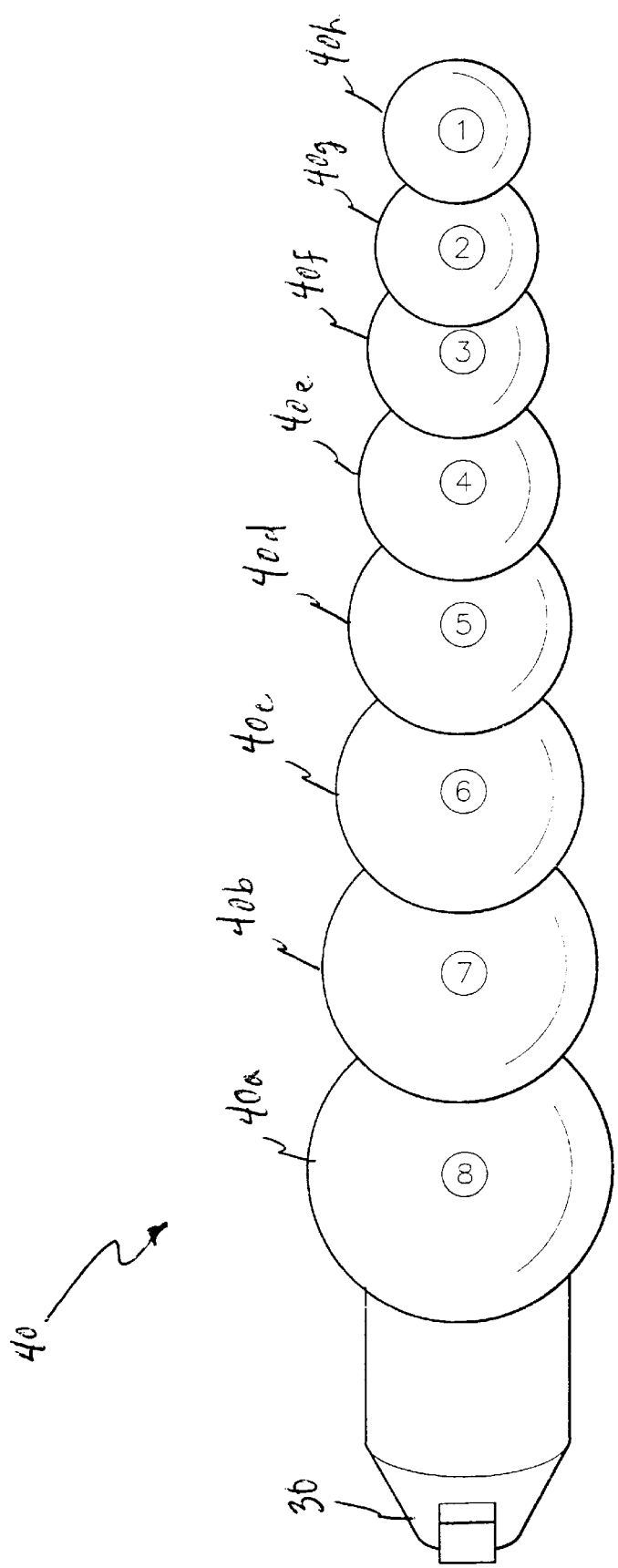
FIG. 2A is a perspective side view of a prosthetic facet member according to a first configuration of the invention.
Figure 2B:
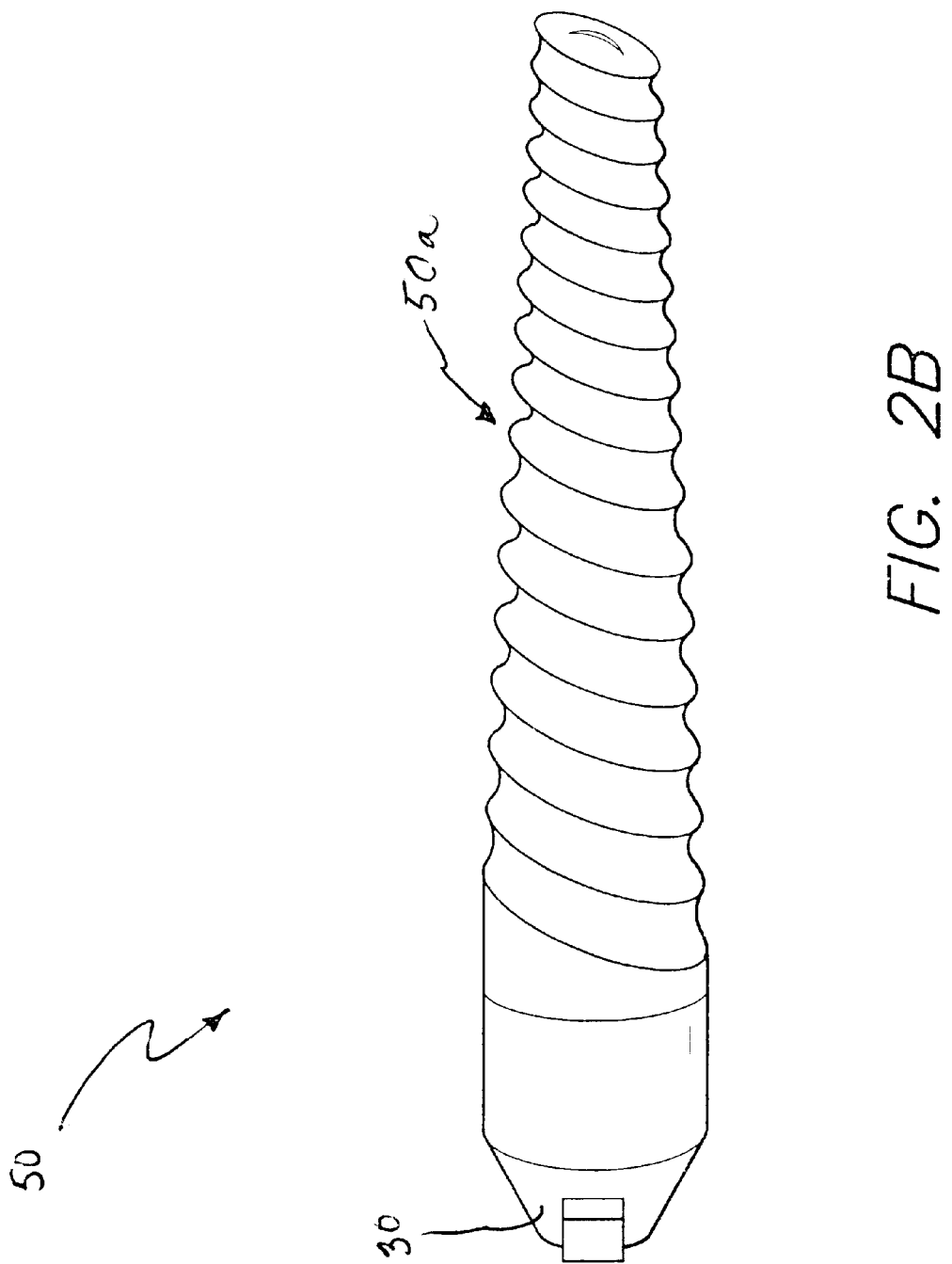
FIG. 2B is a perspective side view of a prosthetic facet member according to a second configuration of the invention.
Figure 2D:
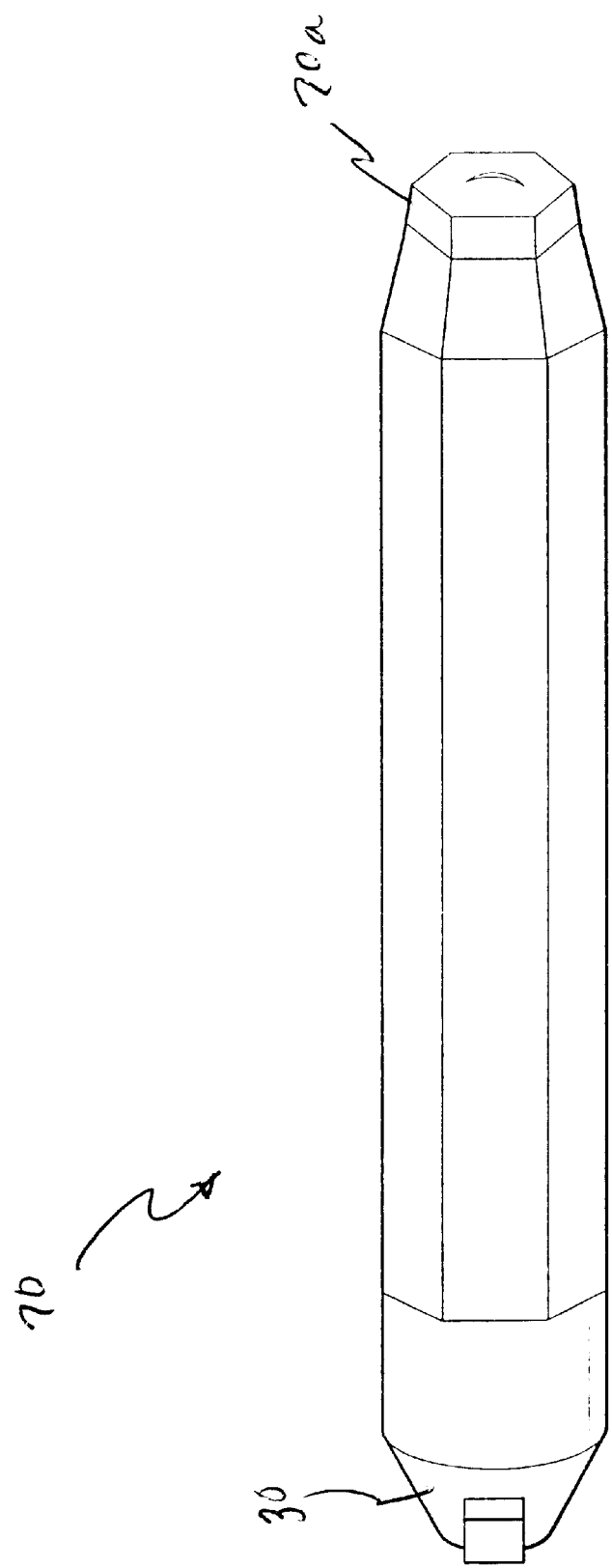
FIG. 2D is a perspective side view of a prosthetic facet member according to a fourth configuration of the invention.
Figure 2E:
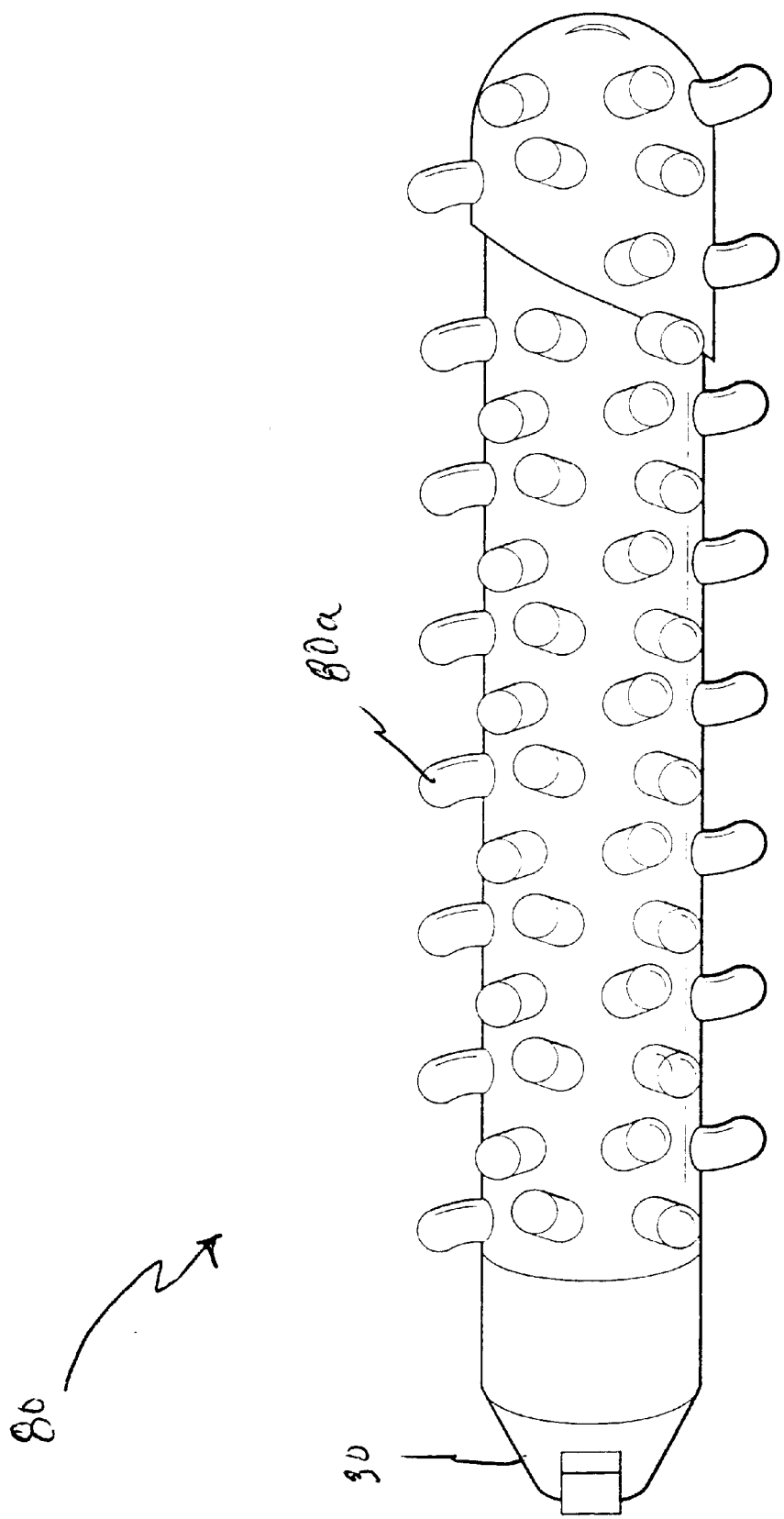
FIG. 2E is a perspective side view of a prosthetic facet member according to a fifth configuration of the invention.
Figure 2F:
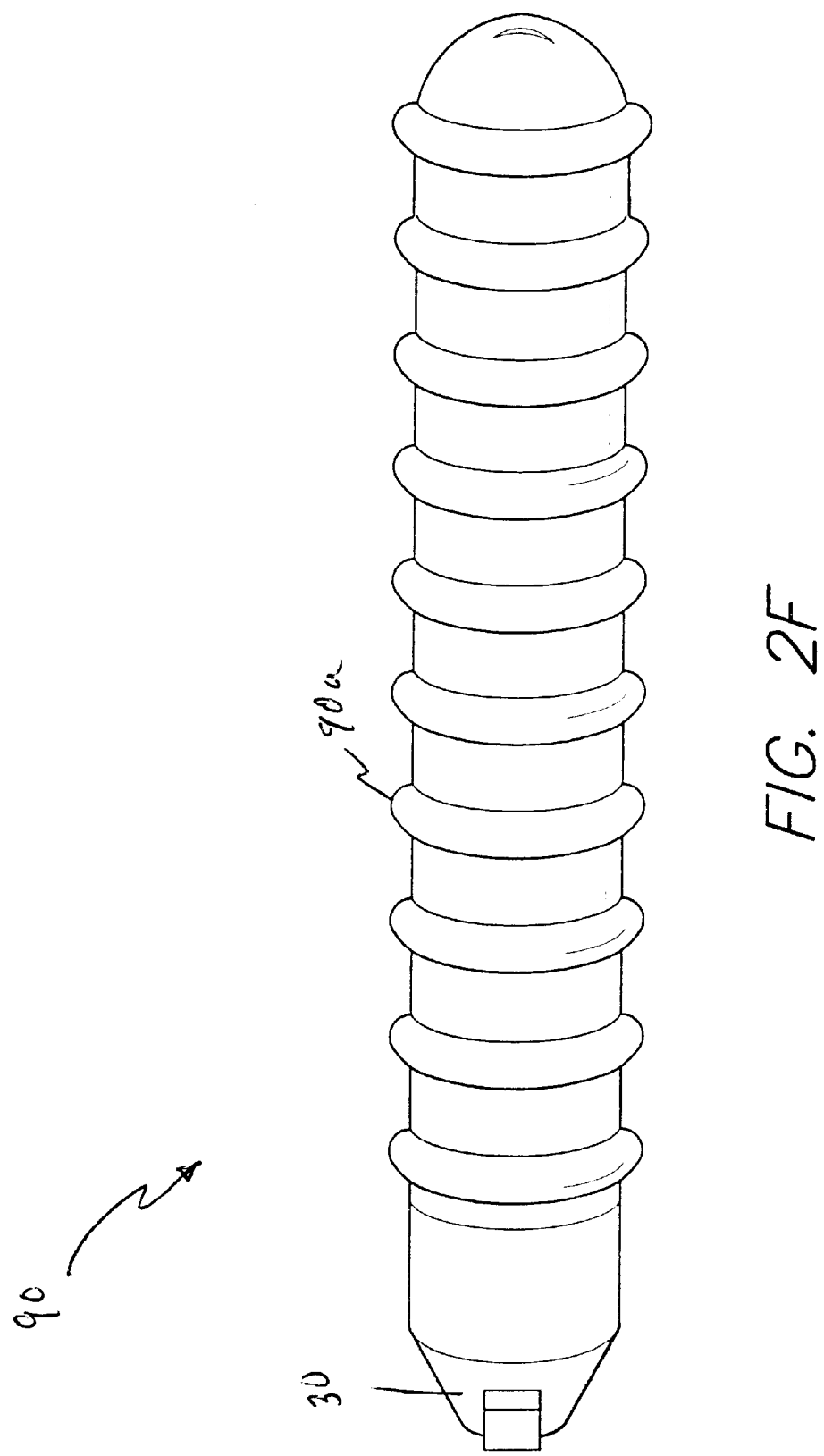
FIG. 2F is a perspective side view of a prosthetic facet member according to a sixth configuration of the invention.

As depicted in FIG. 2D, the phallic element 70 is shown wherein the phallic element 70 is a hexagonal shaped element further including a narrow or tapered distal portion 70a. As depicted in FIG. 2E, the phallic element 80 is shown wherein the phallic element 80 comprises a plurality of peripherally disposed and radial directed cylindrical protrusions 80a. As depicted in FIG. 2F, the phallic element 90 is shown wherein the phallic element 90 comprises a plurality of equally spaced circular rings 90a peripherally disposed thereon.

Figure 3A:
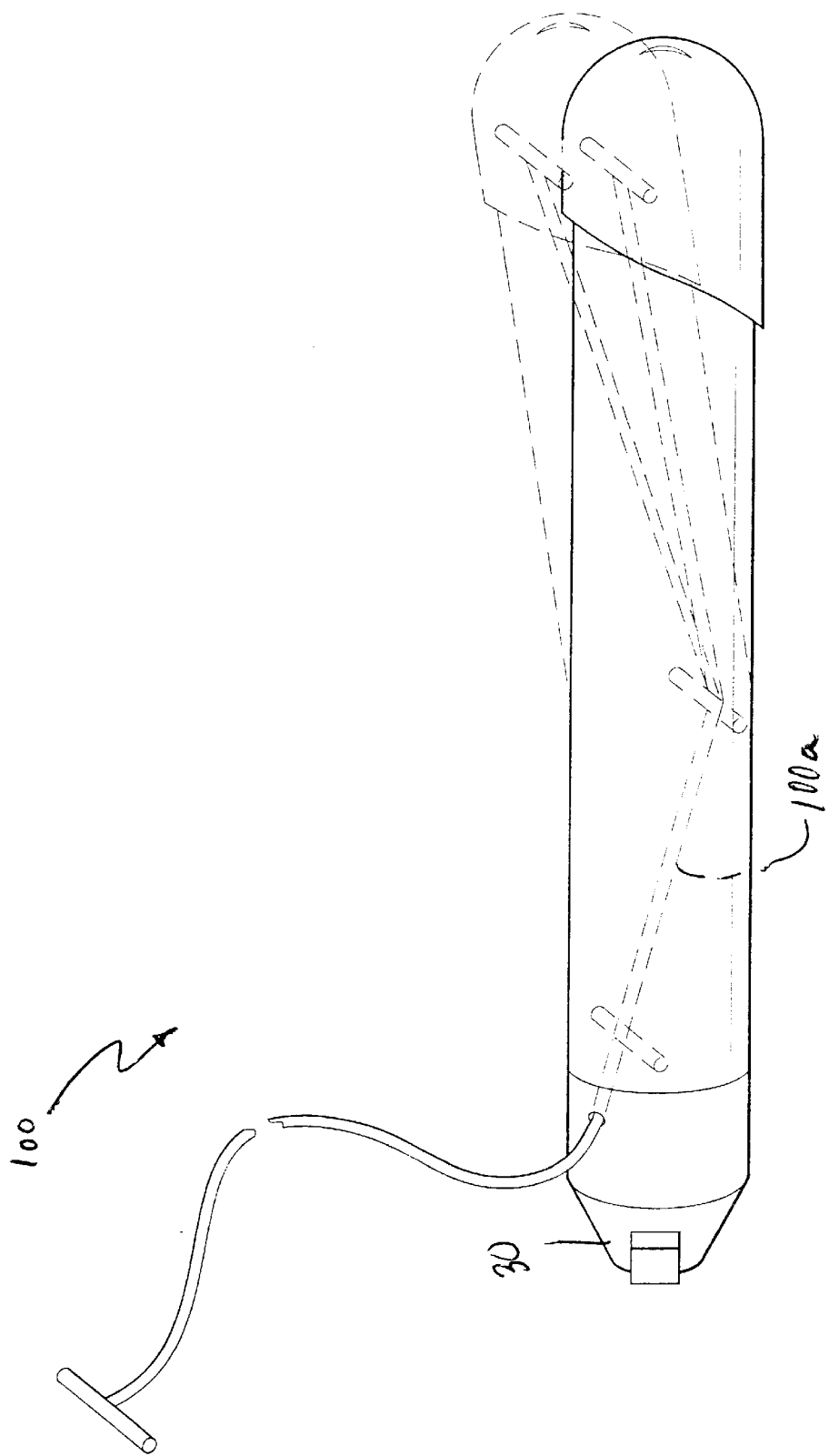
FIG. 3A is a perspective side view of a prosthetic facet member according to a seventh configuration of the invention, illustrating a two-bar linkage controlled facet.
Figure 3B:
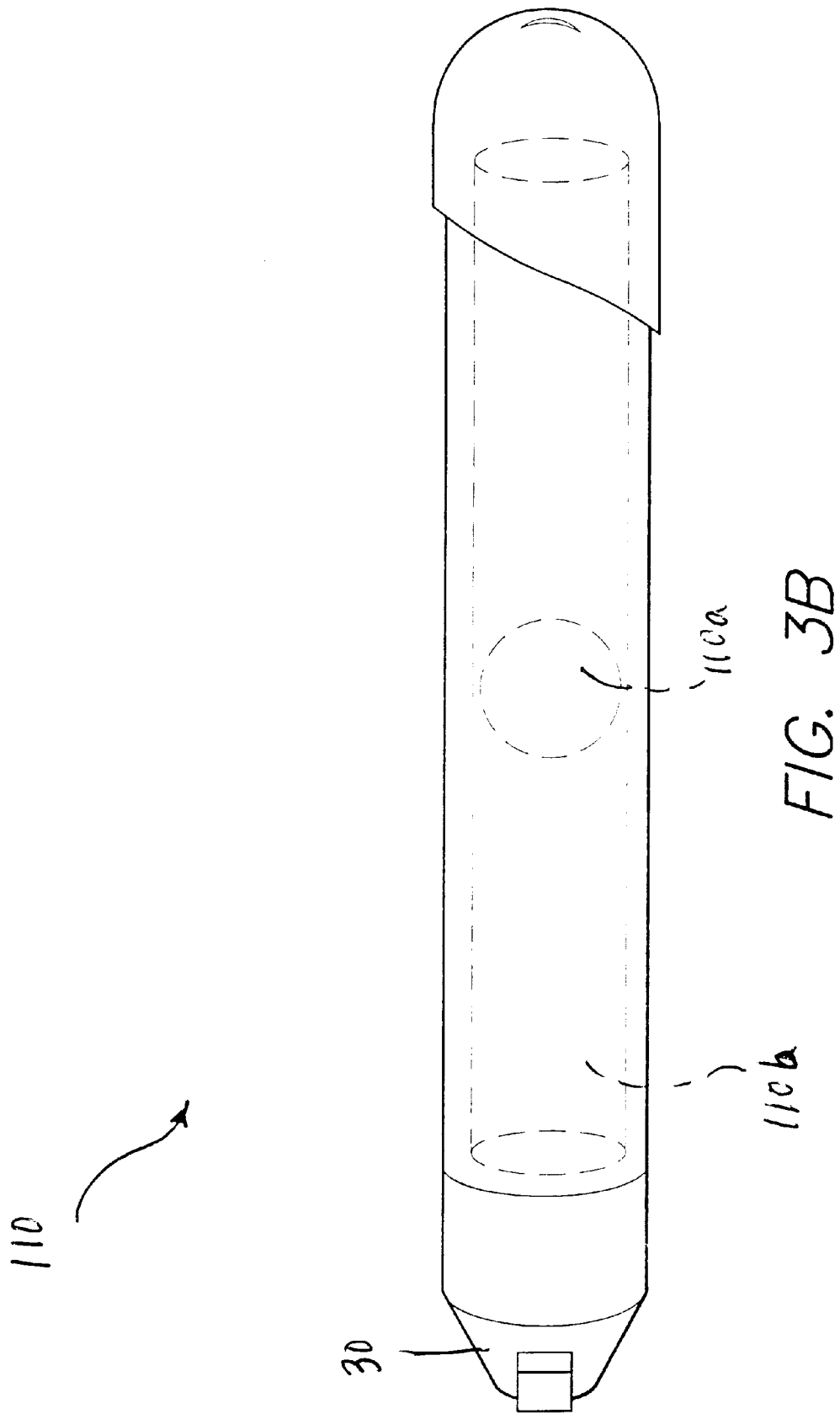
FIG. 3B is a perspective side view of a prosthetic facet member according to an eight configuration of the invention, illustrating a dynamically controlled ball-in-channel facet.
Figure 4A:
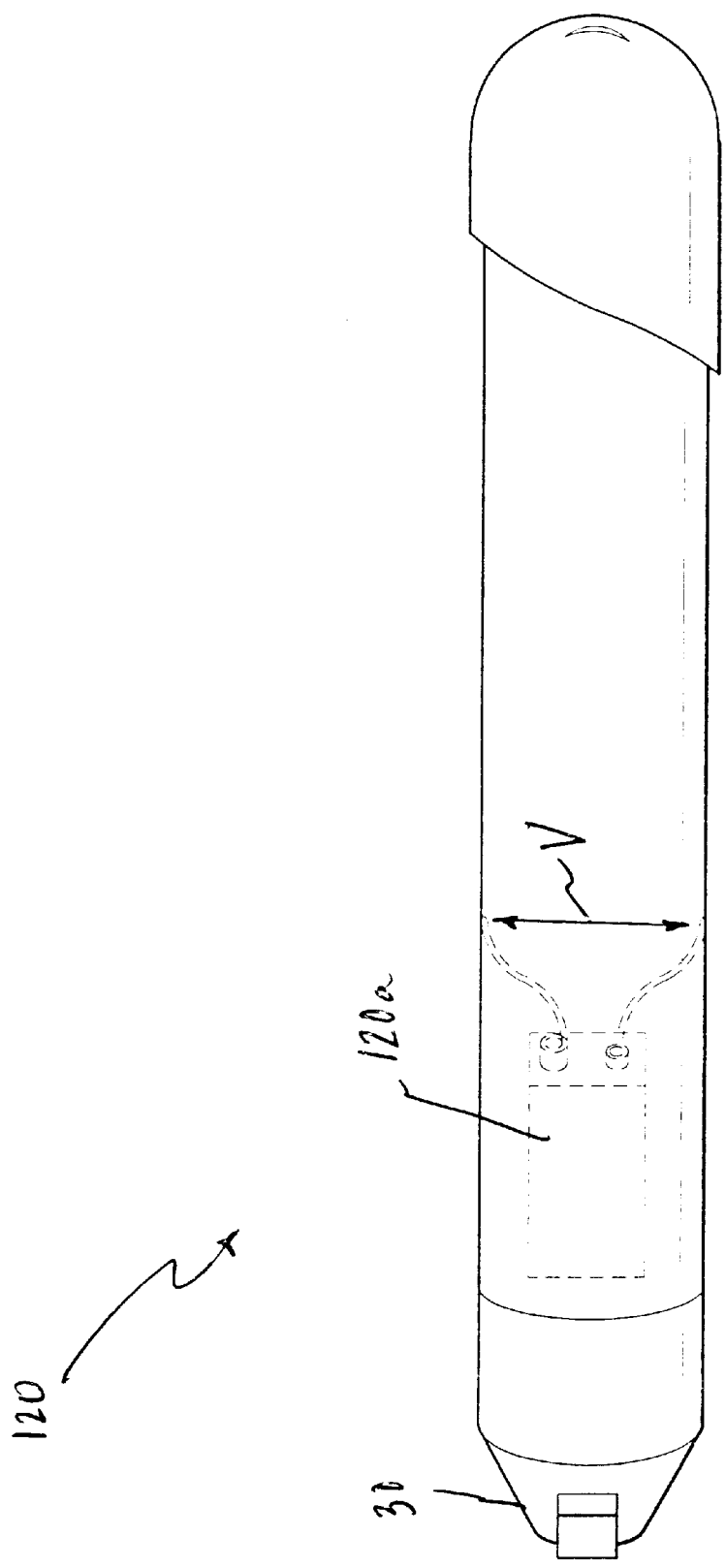
FIG. 4A is a perspective side view of a prosthetic facet member according to a ninth configuration of the invention, illustrating an electric potential generating facet.
Figure 4B:
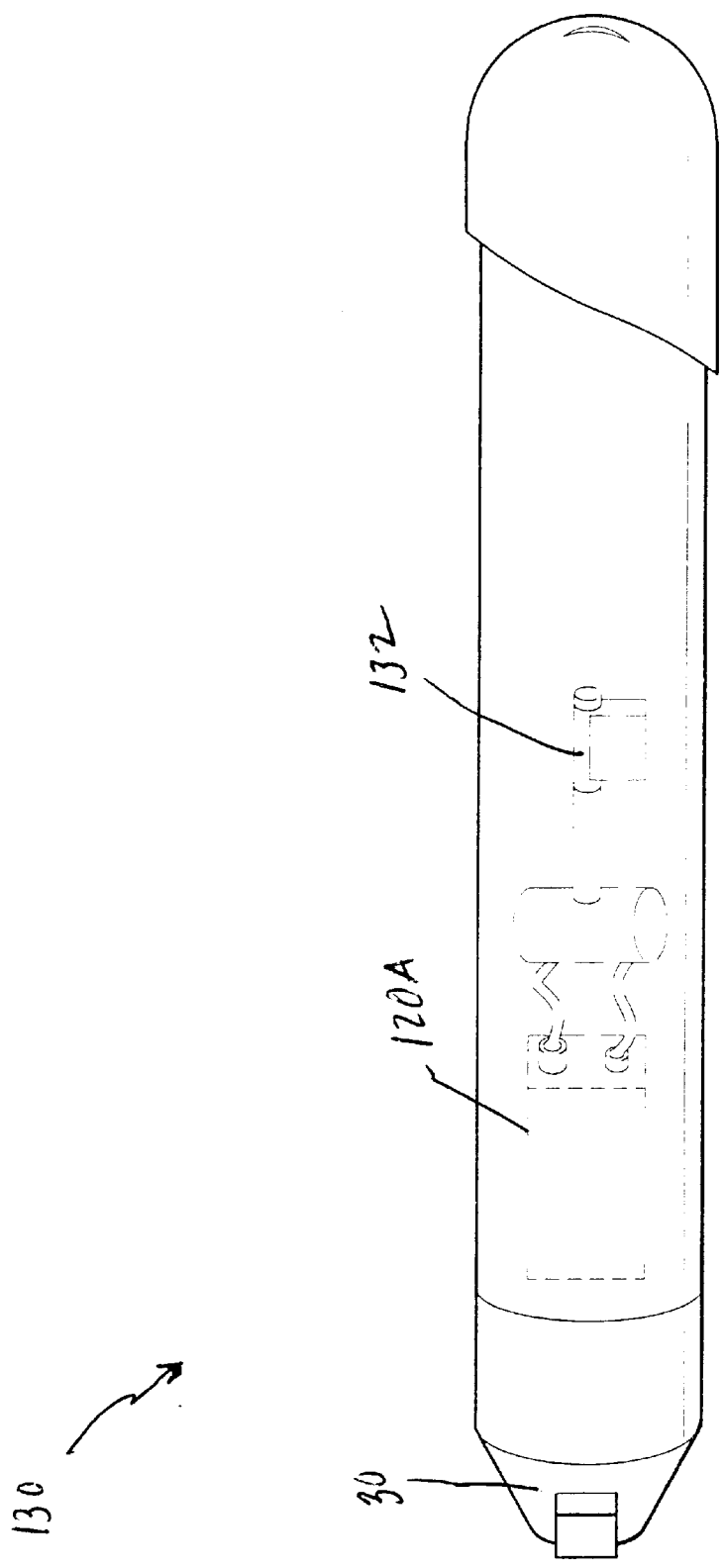
FIG. 4B is a perspective side view of a prosthetic facet member according to a tenth configuration of the invention, illustrating a vibration controlled facet.
Figure 5A:
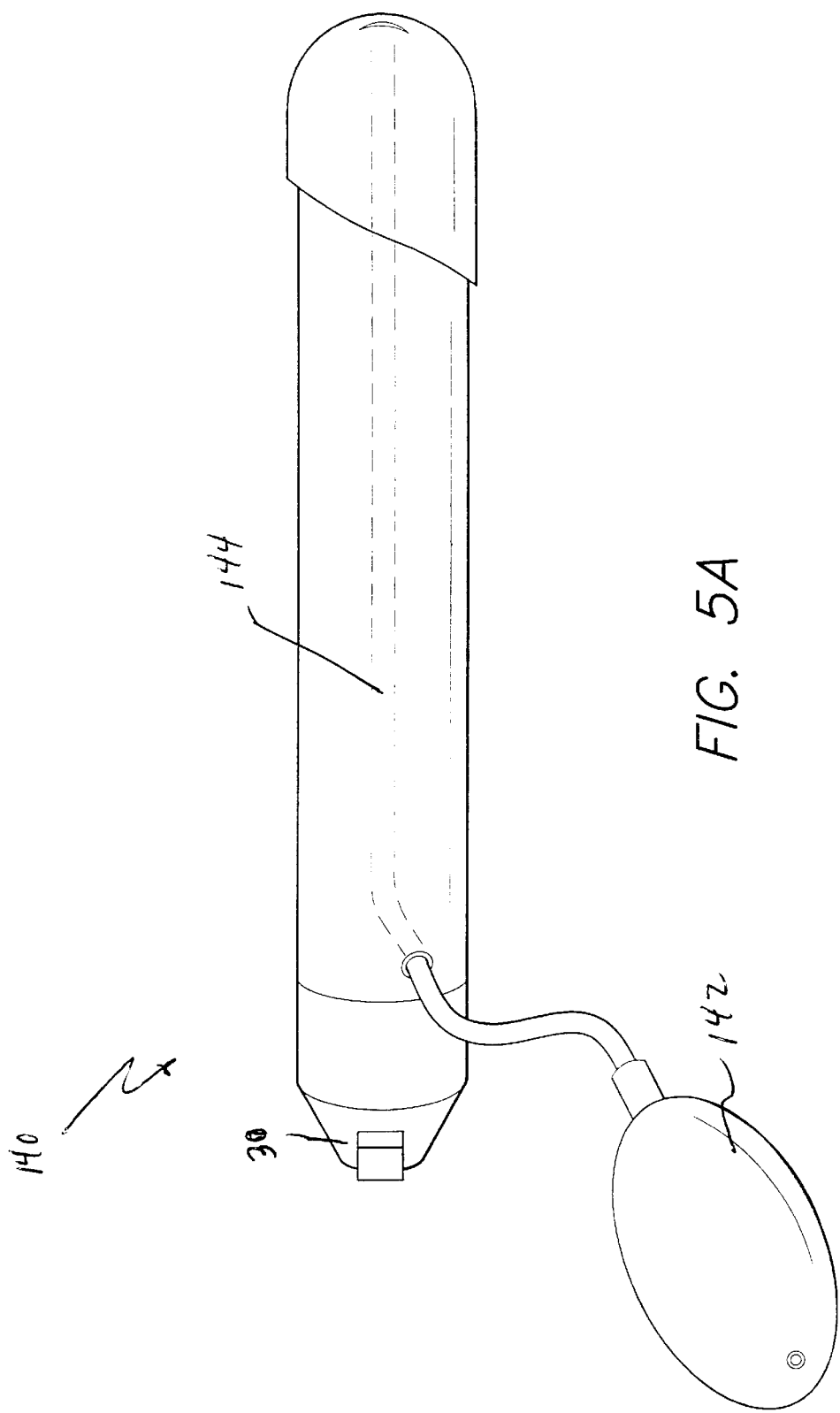
FIG. 5A is a perspective side view of a prosthetic facet member according to an eleventh configuration of the invention, illustrating a fluid projecting facet.
Figure 5B:
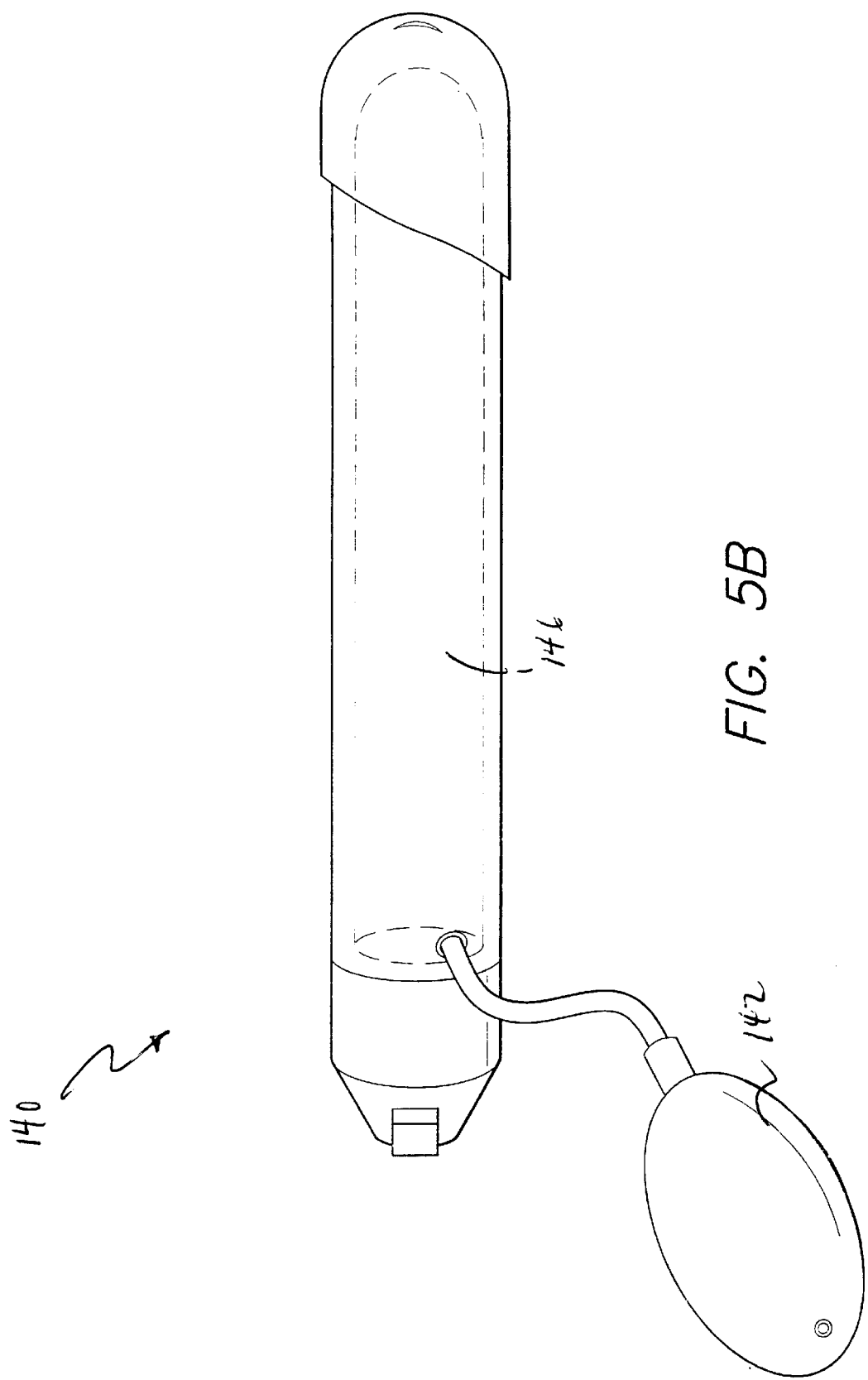
FIG. 5B is a perspective side view of a prosthetic facet member according to a twelfth configuration of the invention, illustrating a fluid retaining facet.
Figure 6:
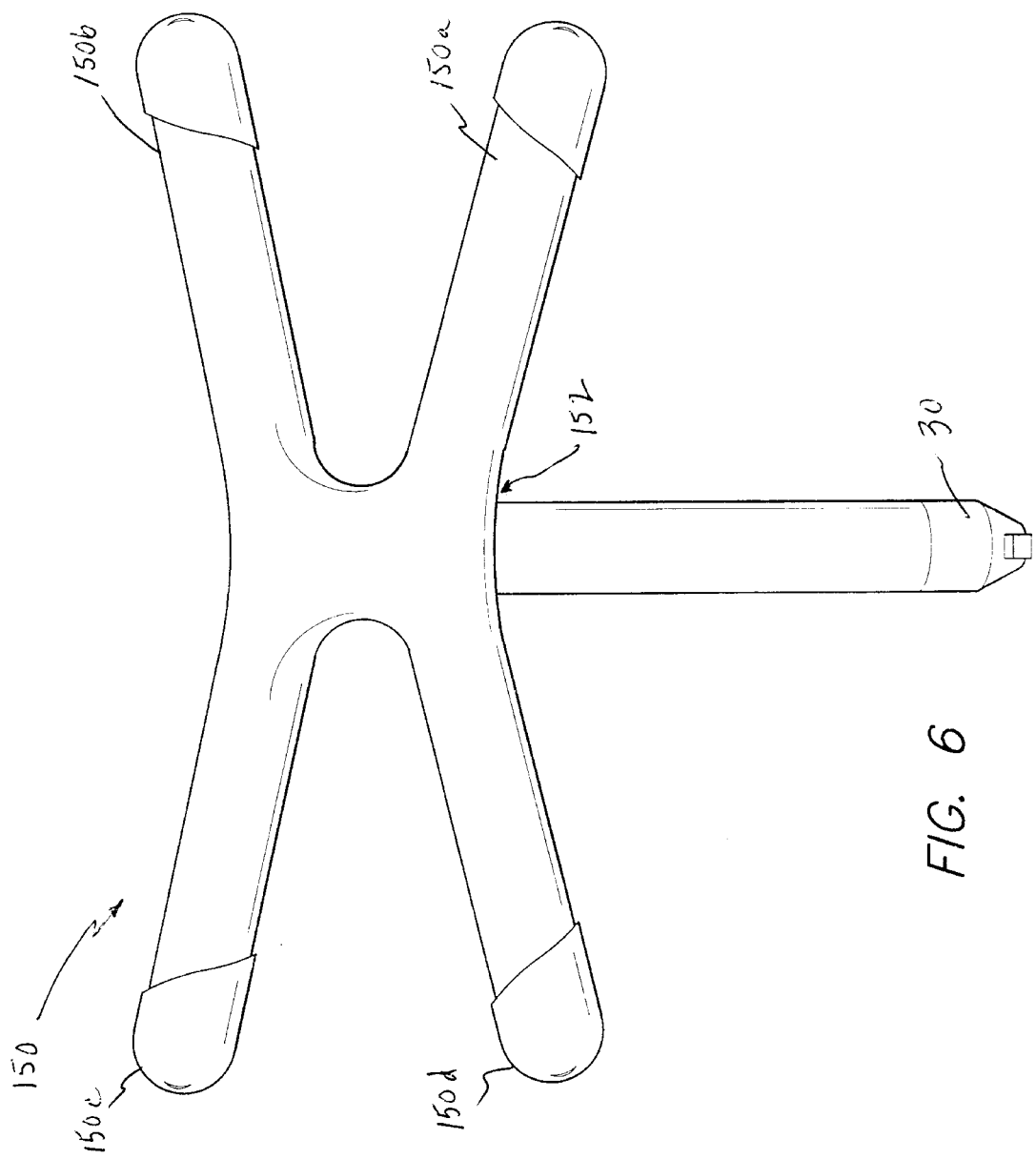
FIG. 6 is a perspective view of a prosthetic facet member according to a thirteenth configuration of the invention, illustrating a multi-prosthetic attachment structure.
Figure 7:
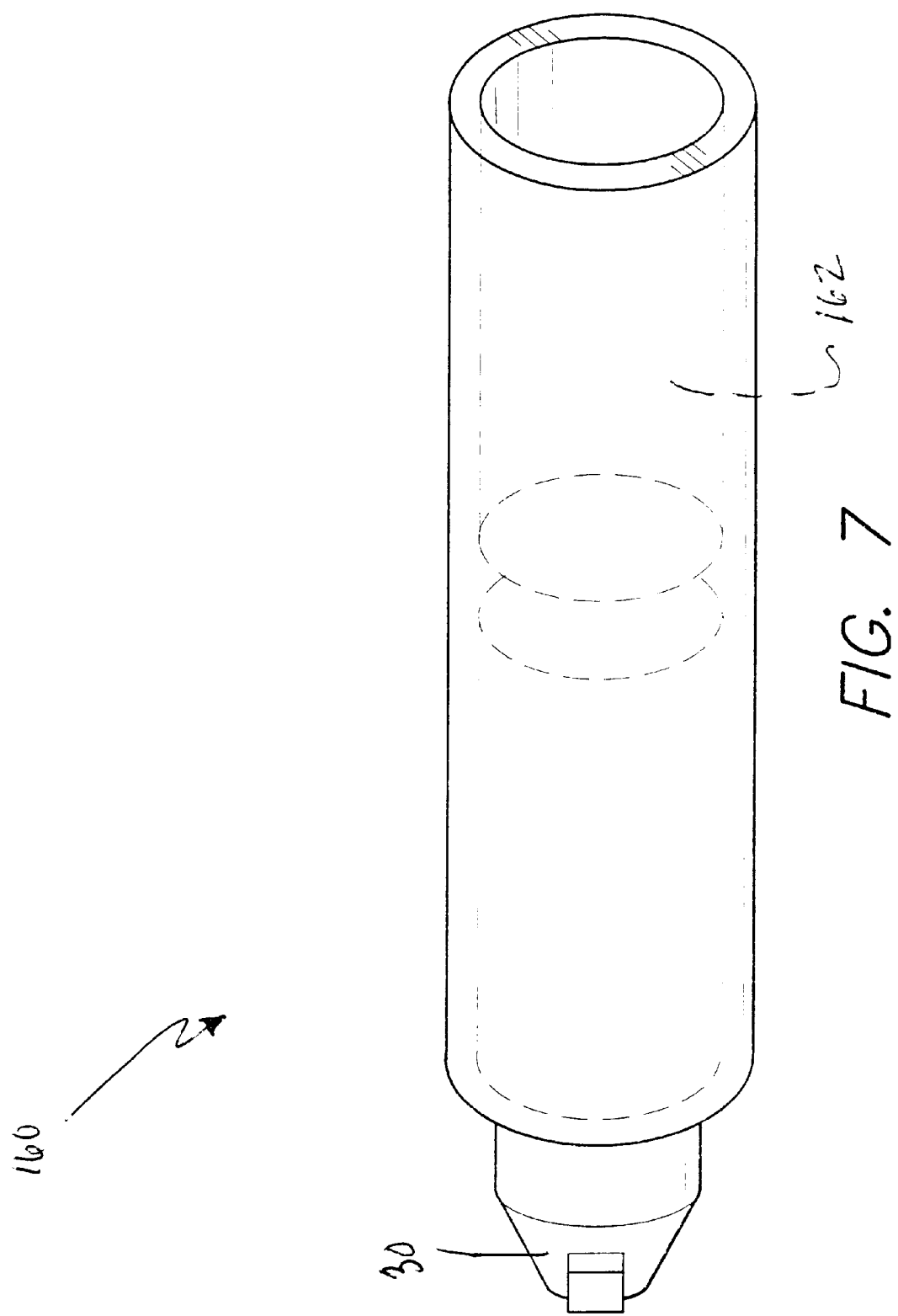
FIG. 7 is a perspective side view of a prosthetic facet member according to a fourteenth configuration of the invention, illustrating an internally disposed cylindrical channel stop.

As depicted in FIG. 3A, the phallic element 100 is shown wherein the phallic element 100 comprises an interstitial two-bar-linkage mechanism 100a. As depicted in FIG. 3B, the phallic element 110 is shown wherein the phallic element 110 comprises a dynamically controlled ball 110a and channel 110b disposed therein. As depicted in FIG. 4A, the phallic element 120 is shown wherein the phallic element 120 comprises a direct current source or battery 120a interconnected therewith for generating a predetermined voltage potential V thereon. As depicted in FIG. 4B, the phallic element 130 is shown wherein the phallic element 130 comprises the direct current source or battery 120a interconnected therewith via a vibratory element 132 for transmitting vibration throughout the phallic element 130. As depicted in FIGS. 5A and 5B, the phallic element 130 is shown wherein the phallic element 130 comprises pump mechanism 142 transmitting fluid through respective channels 144 and 146. As depicted in FIG. 6, the phallic element 150 is shown wherein the phallic element 150 comprises a plurality of interconnected phallic elements 150a, 150b, 150c, 150d disposed on an end 152 having a substantially H-shaped configuration. The last prosthetic configuration is depicted in FIG. 7, wherein the phallic element 160 comprises at least one centrally disposed aperture 162 formed within the length of the element 160.

It is to be understood that the present invention is not limited to the sole embodiments described above, but encompasses any and all embodiments within the scope of the following claims.

We claim:
1. A sexual aid device, comprising:
    (a) a coupler having a cylindrical body and two flared opposing ends, each of the opposing ends defining a concave frustro-conical socket, the socket having a pair of apertures defined therein spaced apart by 180°; and
    (b) at least one prosthetic phallic member having an attachment end, the attachment end having a convex frustro-conical protrusion dimensioned and configured for mating with one of the sockets defined in said coupler, the protrusion further having two spring-biased detents spaced apart by 180°, the detents being dimensioned and configured for interlocking in the apertures defined in the socket;
        wherein said at least one phallic member is detachably connected to one of the opposing ends of the coupler's cylindrical body;

further comprising a belt harness, the belt harness including:
    (a) a waist cincture having opposing ends;
    (b) mating strips of hook and loop fastening material attached to the opposing ends of said cincture for releasable closure of said cincture;
    (c) a loin panel depending from said cincture for covering a lower portion of a pelvis;
    (d) a pair of leg straps, each leg strap having one end attached to said cincture and a second end attached to said loin panel, the leg straps defining loops for accommodating a wearer's legs; and
    (e) a connector attached to said loin panel, the connector forming a frustro-conical protrusion extending from the loin panel dimensioned and configured for mating with one of the sockets defined by the opposing ends of said coupler, the connector further having two spring-biased detents spaced apart by 180°, the detents being dimensioned and configured for interlocking in the apertures defined in the socket;
        whereby a user may strap the harness about the waist, removably attach one end of said coupler to the connector, and removably attach said at least one phallic member to the opposing end of said coupler.

2. The sexual aid device according to claim 1, wherein said phallic member comprises vein like protruding contours along said member.

3. The sexual aid device according to claim 1, wherein said phallic member comprises a series of contiguous spherical balls attached end to end and decreasing in diameter thereto.

4. The sexual aid device according to claim 1, wherein said phallic member comprises a series of concentric spiral contours which taper in decreasing diameter thereto.

5. The sexual aid device according to claim 1, wherein said phallic member comprises a plurality of bumps disposed thereon.

6. The sexual aid device according to claim 1, wherein said phallic member is a hexagonal shaped element.

7. The sexual aid device according to claim 1, wherein said phallic 20 comprises a plurality of peripherally disposed and radial directed cylindrical protrusions.

8. The sexual aid device according to claim 1, wherein said phallic member comprises a plurality of equally spaced circular rings peripherally disposed thereon.

9. The sexual aid device according to claim 1, wherein said phallic member comprises an interstitial two-bar-linkage mechanism.

10. The sexual aid device according to claim 1, wherein said phallic member comprises a dynamically controlled ball and channel disposed therein.

11. The sexual aid device according to claim 1, wherein said phallic member comprises a direct current source interconnected therewith for generating a predetermined voltage potential thereon.

12. The sexual aid device according to claim 11, wherein said direct current source includes a vibratory element transmitting vibration throughout the phallic member.

13. The sexual aid device according to claim 1, wherein said phallic member comprises a pump mechanism transmitting fluid vibration throughout said phallic member.

14. The sexual aid device according to claim 1, wherein said phallic member comprises a plurality of interconnected phallic elements disposed on an end having a substantially H-shaped configuration.

15. The sexual aid device according to claim 1, wherein said phallic member comprises at least one centrally disposed aperture formed within the length of said member.

* * * * *